(12) United States Patent
Schulte et al.

(10) Patent No.: US 6,742,661 B1
(45) Date of Patent: Jun. 1, 2004

(54) WELL-PLATE MICROFLUIDICS

(75) Inventors: Thomas Schulte, Redmond, WA (US); Bernhard H. Weigl, Seattle, WA (US); Chris Morris, Redmond, WA (US); Natasa Kesler, Bothell, WA (US)

(73) Assignee: Micronics, Inc., Redmond, WA (US)

( * ) Notice: Subject to any disclaimer, the term of this patent is extended or adjusted under 35 U.S.C. 154(b) by 33 days.

(21) Appl. No.: 09/932,687

(22) Filed: Aug. 17, 2001

Related U.S. Application Data

(60) Provisional application No. 60/281,114, filed on Apr. 3, 2001.

(51) Int. Cl.[7] .......................... B01D 17/12; B01D 11/00
(52) U.S. Cl. ...................... 210/511; 137/833; 422/68.1; 422/69; 422/100; 422/103; 435/287.3; 435/288.5
(58) Field of Search .......................... 137/833; 422/69, 422/63, 68.1, 99–104; 435/288.4, 288.5, 287.1, 287.3; 210/511, 634; 436/174, 180; 204/451, 453, 600, 601, 604; 428/620, 641

(56) References Cited

U.S. PATENT DOCUMENTS

| | | | |
|---|---|---|---|
| 5,681,484 A | 10/1997 | Zanzucchi et al. | |
| 5,716,852 A | 2/1998 | Yager et al. | |
| 5,869,004 A | 2/1999 | Parce et al. | |
| 5,885,470 A | 3/1999 | Parce et al. | |
| 5,932,100 A | * 8/1999 | Yager et al. | 210/634 |
| 5,971,158 A | 10/1999 | Yager et al. | |
| 5,976,336 A | * 11/1999 | Dubrow et al. | 204/453 |
| 6,103,199 A | 8/2000 | Bjornson et al. | |
| 6,153,073 A | 11/2000 | Dubrow et al. | |
| 6,485,690 B1 | * 11/2002 | Pfost et al. | 422/102 |
| 6,589,729 B2 | * 7/2003 | Chan et al. | 435/4 |

FOREIGN PATENT DOCUMENTS

| | | |
|---|---|---|
| WO | W09700442 A | 1/1997 |
| WO | W09737755 A | 10/1997 |
| WO | W09816315 A | 4/1998 |
| WO | W00017624 A | 3/2000 |

* cited by examiner

*Primary Examiner*—Joseph Drodge
(74) *Attorney, Agent, or Firm*—Seed IP Law Group PLLC

(57) ABSTRACT

Microfluidic devices and methods for performing a microfluidic process are presented. A microfluidic device conforms with a standard well plate format. The device includes a well plate comprising a plate and an array of wells formed on or in the plate, and a microfluidic structure connecting at least two of the wells. The device can rely exclusively on gravitational and capillary forces that exist in channels within the microfluidic structure when receiving fluid streams. Also disclosed is a microfluidic device having an array of microfluidic structures, each connecting at least two wells of a well plate, and connecting three or more wells in alternative embodiments. With the present invention, a large number of microfluidic processes or reactions can be performed simultaneously.

20 Claims, 9 Drawing Sheets

96 WELL CARD

UNIT CELL

WELL-PLATE MICROFLUIDICS

CROSS-REFERENCE TO RELATED APPLICATION

This application claims the benefit of U.S. Provisional Patent Application No. 60/281,114 filed Apr. 3, 2001.

BACKGROUND OF THE INVENTION

This invention relates to microfluidic platforms. In particular, this invention provides microfluidic devices and methods adapted for use with standard well plate filling and reader systems.

Microfluidics relates to one or more networks of microscale channels in which a chemical or molecular process or reaction takes place by virtue of fluidic properties at such scale. The terms "microscale" and "microfluidic" typically refer to fluids provided to channels having internal dimensions of between 0.1 and 500 micrometers. While the utilization of fluidic properties in microscale platforms is relatively well-established, enhancements and the discovery of new properties are continually being made.

Certain well plate formats have achieved widespread use as a standard in the biotechnology and pharmaceutical industry sectors for high-throughput medical diagnostics, drug screening, and other applications where fairly simple chemical analysis processes are performed on multiple samples in parallel. One area that has received some attention is the trend toward fabricating microfluidic platforms to increase throughput, for performing a large number of processes or reactions simultaneously.

Multi-parallel microfluidic platforms would allow more complex chemical processes to be performed in a high-throughput mode in much the same way as more simple chemical processes can be performed with well plate formats. A recent development toward this trend is a microfluidic platform that is compatible with a standard well-plate format. Significant improvements in the number of processes or reactions that can be accomplished have been made by developing microfluidic platforms that conform to a well plate standard format.

Despite development in this area, however, numerous problems exist. Other well plate-compatible microfluidic devices do not provide a fluidic connection from one well to another well, let alone fluidic connection among three or more wells. Further, recent microfluidic devices lack an interface, in combination with two or more wells, in which diffusion or extraction can take place. One such interface is known as a laminar fluid diffusion interface (LFDI), and is formed when two or more fluid streams flow substantially in parallel in a single microfluidic structure.

Another shortcoming of recent well plate-adapted devices is their complexity, both of construction and of use. Most such devices require two or more plates that must be somehow mated together. Each plate must conform to the well plate dimensions, giving rise to mating and alignment problems. Still another problem is how to connect the wells in a well plate with the microfluidic channels in a device.

DETAILED DESCRIPTION OF THE PREFERRED EMBODIMENTS

The above-mentioned shortcomings, as well as other problems, are overcome by this invention. Specifically, this invention provides a relatively simple microfluidic platform that conforms to a standard well plate format, and which maximizes the fluid interfaces within which many microfluidic processes or reactions can be performed, without the need for electrodes or voltage. This invention can be adapted for use entirely with gravitational and capillary forces that exist in microscale fluid channels, and utilizes properties that exist in fluids at such as scale.

This invention relates to microfluidic platforms that are compatible with common well-plate formats (e.g., having an array of 6, 12, 48, 96, 384, or 1536 wells). A microfluidic platform can include a network of microscale channels, inlets, outlets, containers, and other structures. For example, and incorporated by reference herein, U.S. Pat. No. 5,932,100 to Yager et al. describes planar microscale fluid filters, called "H-filters," that capitalize on properties existing at an LFDI. Also incorporated by reference herein, U.S. Pat. No. 5,716,852 to Yager et al., describes several microfluidic differential extraction devices, known as "T-Sensors," where extraction is generated within an LFDI.

These microfabricated structures can also be adapted for performing sample separation, diffusion or cleanup using microscale fluid properties that exist in an LFDI. LFDIs have been specifically applied, among many other applications, to DNA desalting, extraction of small proteins from whole blood samples, and detection of various constituents in whole blood. Other applications include the uniform and controlled exposure of cells to lysing agents, thus allowing any of a number of differentiations of cells by their sensitivity to specific agents. Specifically, these differentiations can be controlled in an on-chip microfabricated cytometer coupled directly to the lysing structure.

One H-Filter can be connected to at least two wells. H-Filters are configured to move fluid through a channel according to a pressure differential between inlets and outlets. These H-Filters can be operated in several ways. In one configuration, the H-Filters are driven by hydrostatic pressure. The wells are filled to different levels to produce a variable level of hydrostatic pressure for the H-Filters. In alternative configurations, the H-Filters can be interfaced with a pressure source, such as an array of pressure transducers, or an array of displacement pumps. Additionally, the wells of the well-plate can be manufactured to have different or variable bottom levels, allowing for wells connected to H-Filter inlets to completely drain through the H-Filter into wells connected to H-Filter outlets. Other configurations for the microfluidic structures include T-Sensors having one or more inlets connected to a common microfluidic channel, and at least one outlet.

Figure 1:
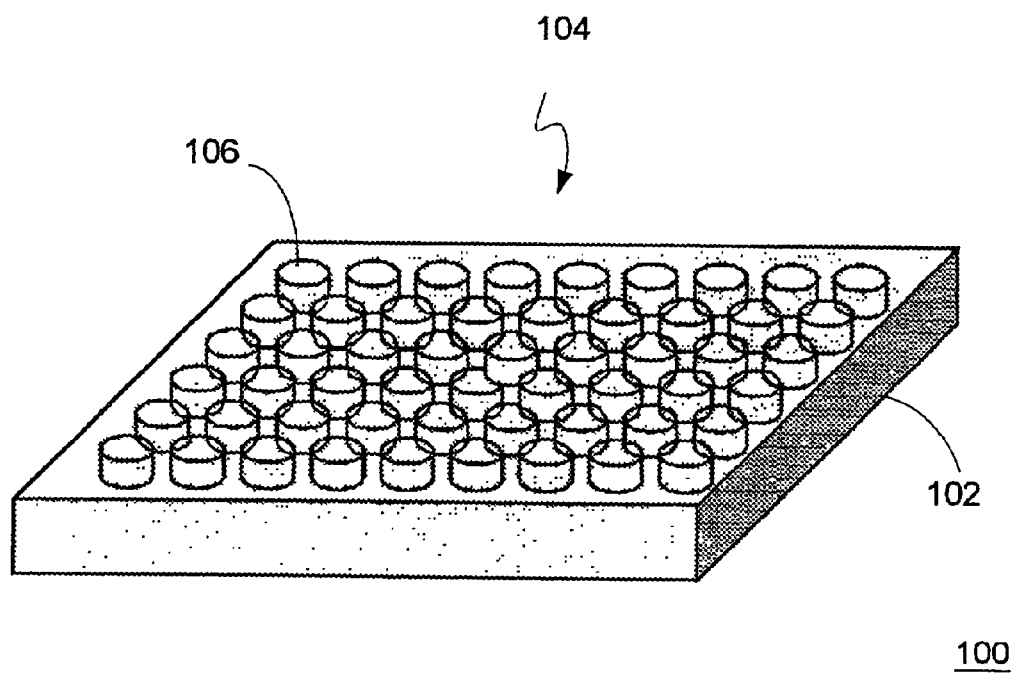
FIG. 1 shows a standard well-plate.

FIG. 1 depicts a well plate 100, conforming to a standard well plate, which is also commonly known as a microtiter plate. The well plate 100 includes a plate 102 and a patterned array 104 of wells 106. The wells 106 can be formed in the plate 102, or can be formed on the plate in a separate layer overlying the plate 102. Each well 106 preferably has a cylindrical or conical shape, or, alternatively, a rounded shape. The circumference and/or shape of each well 106 may also be angular.

A well plate 100 having 96 wells patterned in a planar, two-dimensional array is the most common standard in the pharmaceutical industry for biological and chemical analysis and testing. Other numbers and arrangements of the patterned array 104 of wells 106 are possible. For example, other standard well plates 100 exist with 6, 12, 24, 48, 192, 384, 1536, or more, wells 106. Further, while a standard array has a linear M-row by N-column pattern of wells, the wells 106 can also be arranged according to other patterns to accommodate different robotic filling systems, for example.

Figure 2:
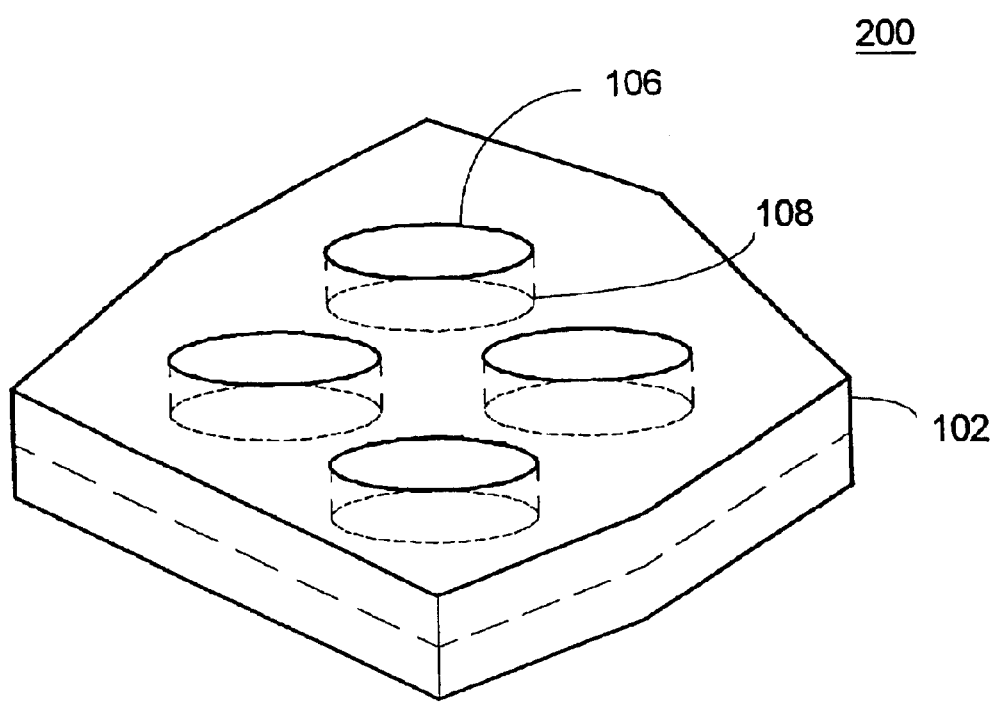
FIG. 2 is a sectional view of a well-plate shown in FIG. 1 to illustrate the wells formed on or in the plate.

FIG. 2 is an exploded view of a portion 200 of a well plate as shown in FIG. 1. The plate 102 may be formed of one or more layers of a material. The material can be metal, plastic, glass, or any other rigid or semi-rigid material. Multiple layers can be fused, glued or otherwise affixed together. Each well 106 is formed to a particular dimension and/or volume, defined in part by a bottom 108. The shape of the well 106 and bottom 108 are formed such that the well 106 has a specific volume and/or fluid displacement or flow rate. A bottom 108 of one well 106 may be relatively higher or lower in a plane as a bottom 108 of at least one other well 106 on the plate 102, also to allow for different rates of flow and/or volume. In sum, the shape, bottom 108, volume, relative depth, and other factors pertaining to each well 106 can be configured for a particular application.

Figure 3:
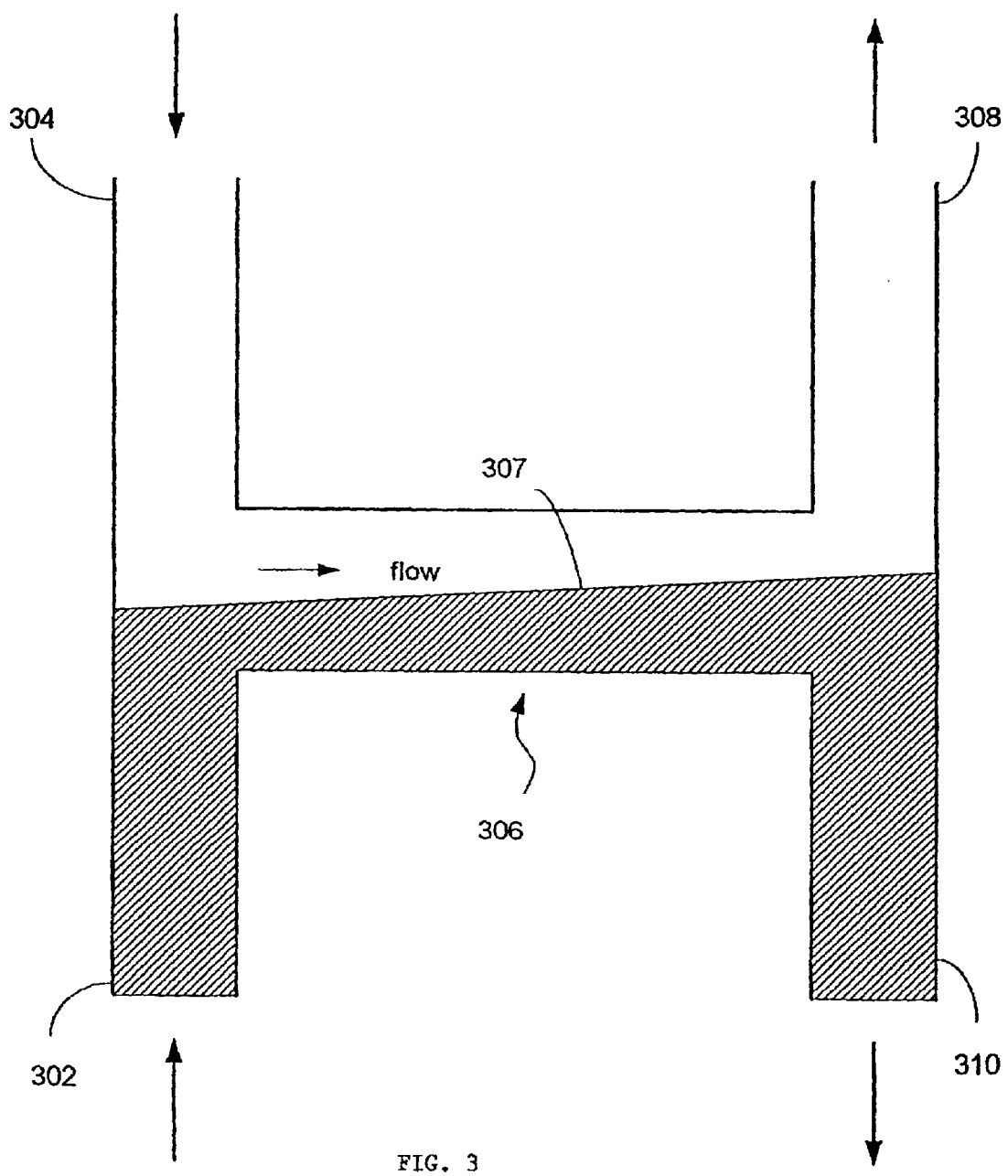
FIG. 3 shows an H-Filter-type microfluidic structure.

FIG. 3 illustrates one type of microfluidic structure 300, embodied as an H-filter. Microfluidic structure 300 has a first inlet 302 and a second inlet 304 connected to a channel 306, which is in turn connected to a first outlet 308 and a second outlet 310. The H-filter is so-called because of its general "H" shape. However, each of the inlets, outlets, and channel of the microfluidic structure 300 can be formed to any shape or orientation. For example, in order to lengthen the channel 306, the channel 306 can be formed into a curve or serpentine structure.

A fluid is provided in each of the first and second inlets 302, 304, which flow in parallel in the channel 306, providing an interface 307 at which a process or reaction between the parallel-flowing fluids can take place. It is important to note that the first and second inlets 302 and 304 are preferably oriented to the channel 306 so as to allow one fluids to flow on top of the other, in order to maximize the interface 307. Thus, the side-by-side flow shown in FIG. 3 is provided for purpose of example only.

The parallel flow of fluids in the channel 306 allows for any number of different types of reactions or processes which take advantage of micro-scale flow properties. For instance, diffusion of particles from one fluid to another will occur between parallel-flowing fluids, based on factors such as temperature, viscosity, etc. The first outlet 308 and second outlet 310 are configured to output a fluid sample of interest, waste, or both. Those having skill in the art would recognize that more or less inlets and/or outlets can be used depending on the microfluidic application or process.

Figure 4:
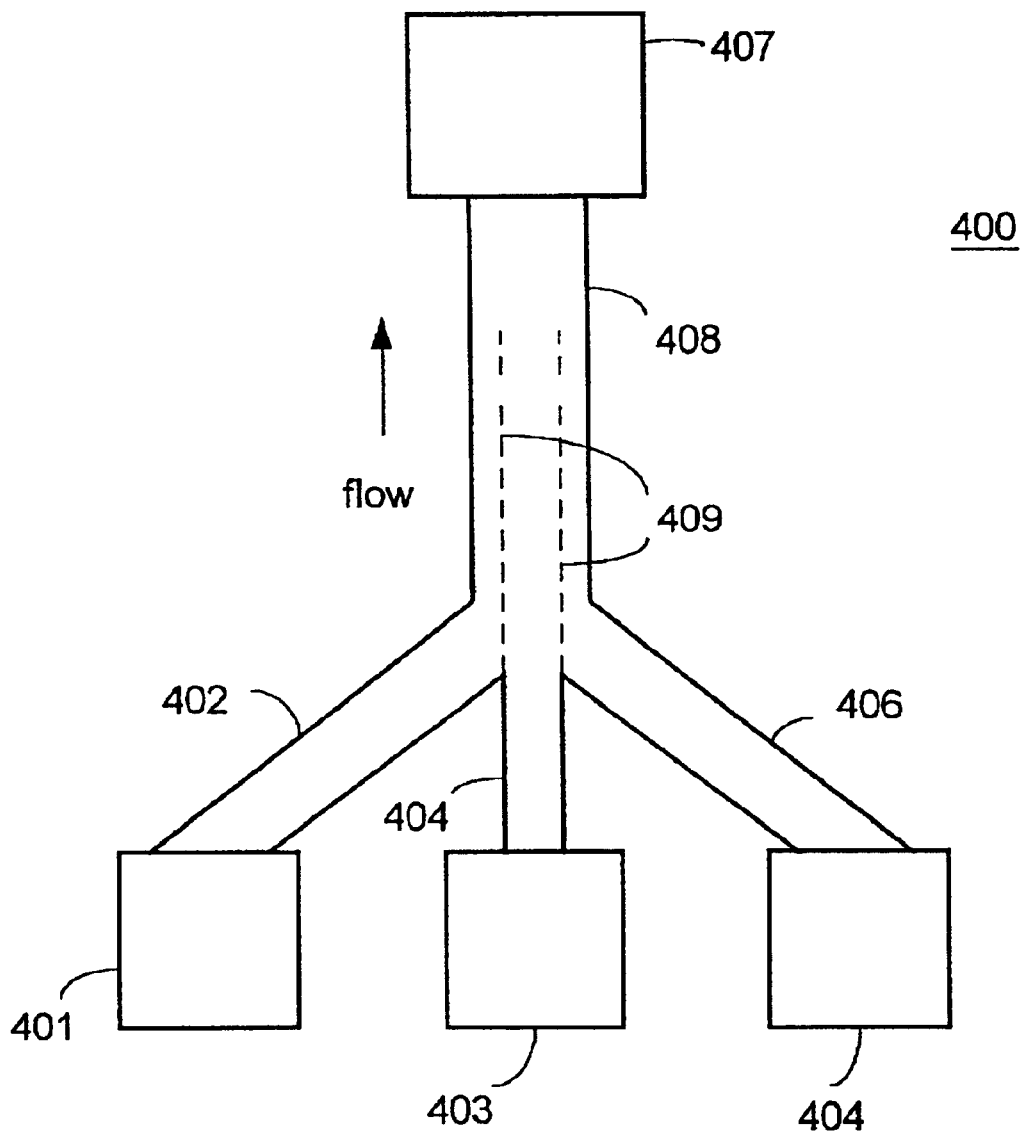
FIG. 4 shows a T-Sensor-type microfluidic structure.

FIG. 4 shows a T-Sensor as another type of suitable microfluidic structure. The microfluidic structure 400 has first, second, and third inlet collectors 401, 403 and 405. The inlet collectors 401, 403 and 405 temporarily store a fluid, and provide the fluid to each of connected inlet channels 402, 404, and 406. The inlet channels 402, 404 and 406 converge to a common channel 408, in which diffusion, absorption or other reactions or processes take place. The parallel-flowing fluids in the common channel 408 are ultimately provided to a waste collector 407.

Those having skill in the art would recognize that the microfluidic structures 300 and 400 illustrated in FIGS. 3 and 4 respectively, are described for the benefit of example only. Many different arrangements of microfluidic structures are possible. For example, with reference to microfluidic structure 400, the length of the common channel 408 can measure from a few microns, to over 10 centimeters or more. Further, the common channel 408 is shown here as linear, but can also be curved, rounded, serpentine, etc. Thus, many variations are possible within the scope of the invention.

Figures 5A, 5B:
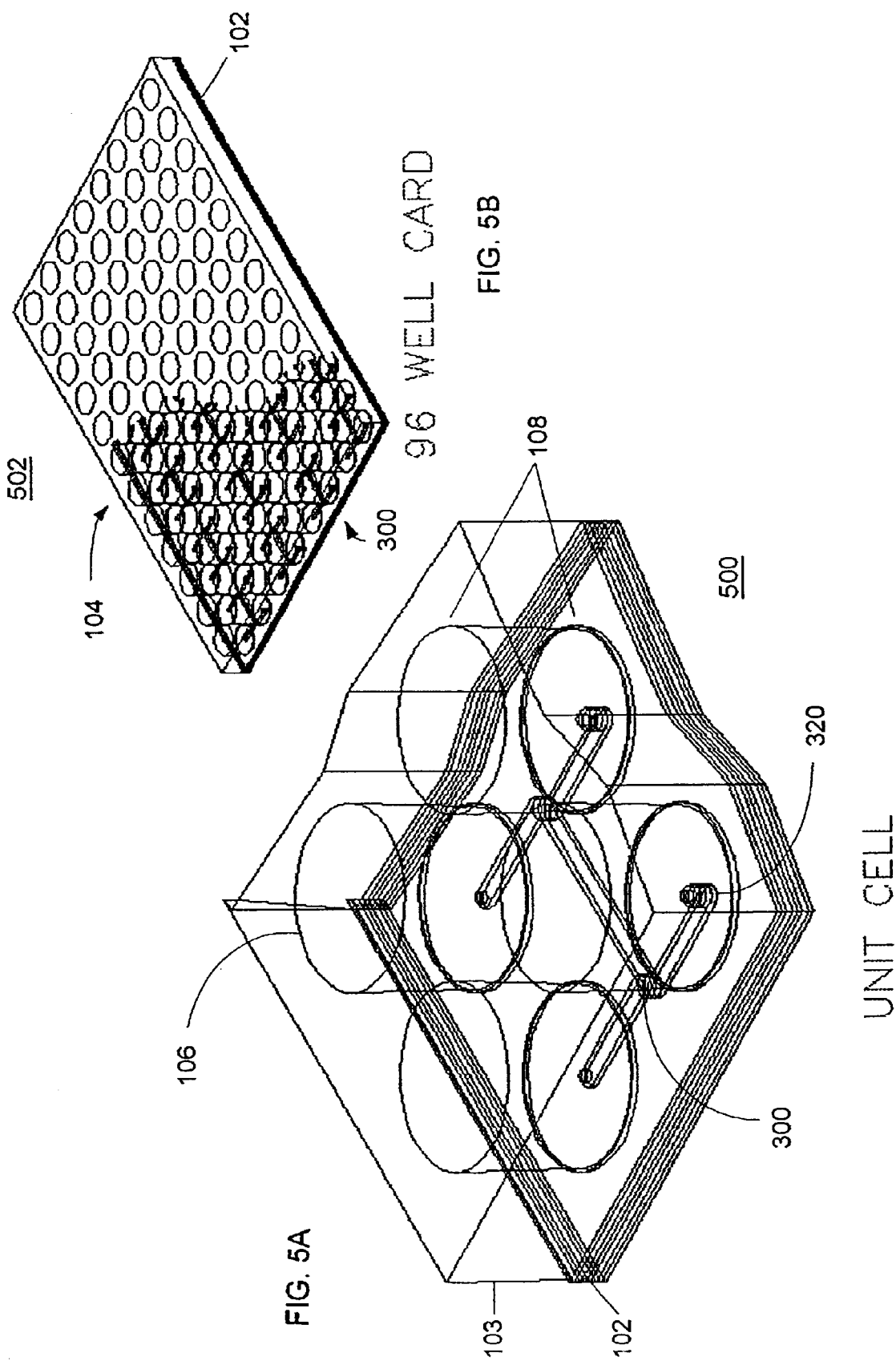
FIGS. 5A and 5B illustrate a microfluidic device having an array of wells and a microfluidic structure connecting at least two of the wells.

FIG. 5A illustrates a section of a microfluidic device 500 having a plate 102, an array of wells 106 formed on or in the plate 102, and a microfluidic structure 300 connected to at least two of the wells 106. The wells 106 and/or microfluidic structure 300 can be formed integral with the plate 102, or into a substrate 103 formed over the plate 102, as illustrated. The microfluidic structure 300 shown is an H-Filter type structure, as discussed above with respect to FIG. 3. The microfluidic structure 300 is shown having two inlets and two outlets, for connecting to four wells 106.

The connection of the microfluidic structure 300 to the wells 106 can be made anywhere which allows fluidic transference between the wells 106 and the microfluidic structure 300. The connection between the wells 106 and the microfluidic structure 300 can made in substantially the center of the bottom of each well 106, and can be made via a port hole 320. The connection may also be made into the side of the well 106 for better optical observation of the well. The port hole 320 connection to a well 106 can also be sized according to a desired flow rate between the well 106 and the microfluidic structure 300.

Fluid from at least one well 106 is provided to the microfluidic structure 300, where a microfluidic process or reaction is performed. For instance, fluid from two wells can flow to a channel via two inlets, where an extraction process occurs. The fluid can be transferred from the microfluidic structure 300 to another well 106 on the same platform, or to another type of collector on the same or different platform, such as another microfluidic channel.

FIG. 5B depicts a microfluidic platform as a microfluidic card 502 to illustrate the integration of a patterned array 104 of wells, selectively interconnected by an array of microfluidic structures 300. In a preferred embodiment, the well plate and array of microfluidic structures are formed in a laminar diffusion interface card using a one-dimensional diffusion model. This model yields optimal concentration of a species as it diffuses into a receiver fluid. The microfluidic platform preferably utilizes gravitational forces and capillary action to promote fluid flow. However, a pressure generating mechanism can be used to apply a controlled pressure to a specific number of wells and the fluid therein, or for increased hydrostatic pressure.

Since the wells 106 of the well plate 102 are limited in height, the achievable hydrostatic pressure in each well can be very low. The low hydrostatic pressure can be overcome by a second plate (not shown) placed over the well plate 102. The second plate can be formed of a heavy, rigid or semi-rigid material. The second plate can include protrusions corresponding to the individual wells 106, for sealing against the side walls of the wells 106. The second plate would provide extra weight, and therefore increased pressure.

A microfluidic process occurs within the microfluidic structure, such as extraction or separation between two parallel flowing fluids or solutions. The hydrostatic driving force will typically be in a direction normal to the plane of the well plate 102. However, the microfluidic device of the invention can be configured such that the well plate 102 can be flipped to various orientations for multiple directions of hydrostatic pressure.

Figure 6:
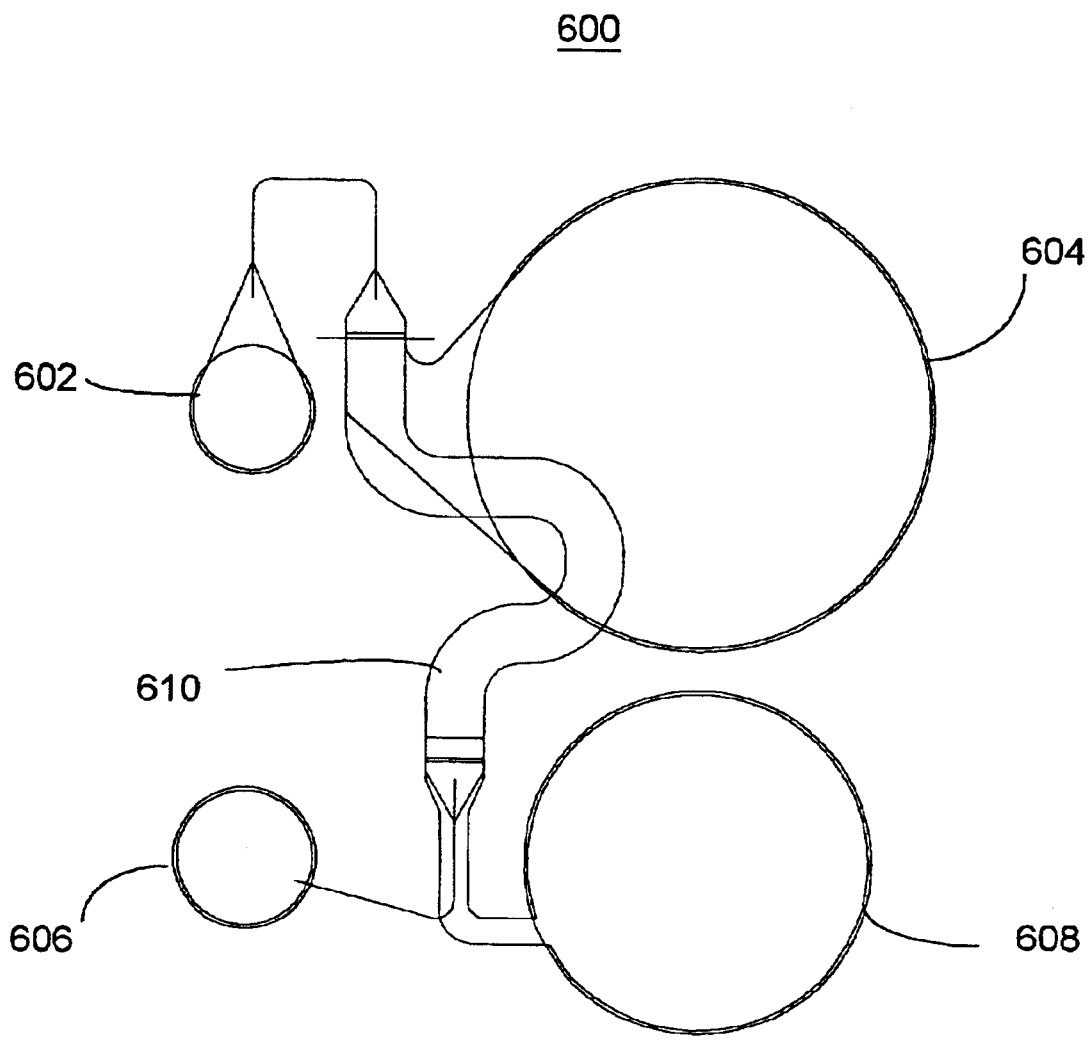
FIG. 6 is a top view of a device showing an embodiment of a microfluidic structure connected to a number of wells.

FIG. 6 is a top plan view of a group of four wells connected by an H-filter, according to a specific exemplary embodiment. A sample well 602 is filled with a first solution containing a sample, such as, for example, a fluorescein and blue dextran. A receiver well 604 is filled with a second solution, such as a clear buffer, for example. The sample well 602 and receiver well 604 are each connected to a microscale channel 610 by an inlet. As depicted, the wells 602, 604 can be formed to a different shape and/or volume so as to achieve a particular rate of flow from the wells. solution into the second solution. A product from the microfluidic process is collected at a product well 606. For instance, in the example, the product well 606 receives the blue dextran and a lower concentration of the fluorescein. A waste well 608 receives a waste solution from the microfluidic process, such as the fluorescein extracted from the first solution. The product well 606 and waste well 608 are connected to the channel via outlets. The wells 606 and 608 can also be formed to a particular size and/or volume, respective or not to the other wells, to achieve a certain in-flow rate.

A similar structure, having one or more outlet wells, can also be used to perform a chemical reaction between chemical components contained in two fluids. The product of this chemical reaction can then be observed, or its concentration measured, in the outlet well. This structure can also be used to monitor a chemical reaction in a different way using the T-Sensor. Two fluids will flow next to each other in a microfluidic structure while the chemical components contained in each of the fluids will diffuse into each other. The reaction product is formed in this diffusion interaction zone, and can be observed through the bottom of the plate. The intensity, width, and other properties of this zone can be proportional to the concentration of the reaction product.

A microfluidic platform can be contained in a single card, with the same form factor as a standard well plate. The microfluidic platforms are implemented as low-cost, plastic disposable integrated circuits, where each circuit includes one or more microfluidic structures. According to one embodiment, the microfluidic circuits are formed of laminates built of individually cut or stamped fluidic circuits. The lamination process yields complex 3-dimensional structures. The lamination process can include a number of layers of different types of thin plastic sheets, preferably ranging in thickness from about 10 micrometers to a few hundred micrometers. The layers can be bonded together using an adhesive, or by a thermal bonding process. In ranging in thickness from about 10 micrometers to a few hundred micrometers. The layers can be bonded together using an adhesive, or by a thermal bonding process. In some cases, the internal surfaces of the laminates can be chemically treated, e.g. with oxygen plasma, to change their wettability.

The microfluidic structures and circuits can be first modeled using a fluid modeling software package. The modeling takes account of fluid properties at microscales. Since fluid dynamics at this scale is computationally intensive, simpler models may be used based on a series solution for cases where the flow field and related properties are known. The microfluidic structures can then be designed using a computer-aided design software program. For instance, one microfluidic circuit can contain up to 12, or more, layers, the collective layout of which is indexed as a "cut file." The plastic is subjected to a cutting mechanism, such as a laser cutter, for forming the channels and circuits according to each cut file.

In specific preferred embodiments, channel dimensions can range from 100–3000 $\mu$m in width, and from 500–400 $\mu$m in depth. Typically, the lower limits of these dimensions are defined by the size of the largest particles to be passed through a channel, whereas upper limits are set by the requirements for laminar flow, and the need to provide sufficiently small diffusion dimensions between adjacent streams flowing in parallel. Accordingly, these dimensions are mentioned for exemplary purposes only, and not by way of limitation.

Other fabrication processes may be employed, such as hot embossing, micro-injection molding, and silicon or glass lithographic techniques. While the embodiments described above function without power or external forces, the fabrication process outlined above allow for incorporating hybrid elements into the design of the microfluidic devices, such as electrodes, filter membranes, and sensors, etc.

Figure 7:
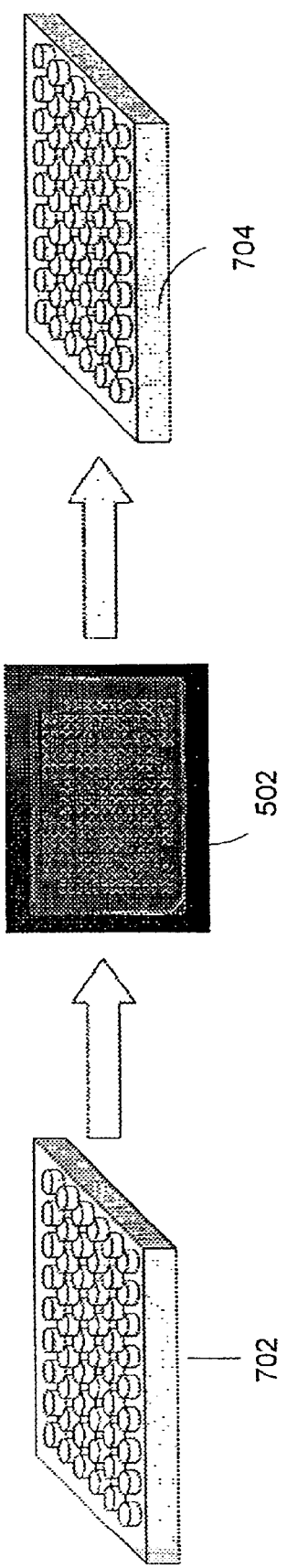
FIG. 7 illustrates a microfluidic process using a microfluidic device in combination with a standard well plate.

FIG. 7 illustrates several processes in which a microfluidic card is used in conjunction with one or more standard well plates. A first standard well plate 702 is used for an initial reaction. The first well plate 702 can be accessed and loaded robotically, according to any one of several known or new mechanisms. Then, the first well plate 702 is contacted with a microfluidic platform 502 card, in which a microfluidic operation or process is performed. Then, the microfluidic platform 502 is contacted with a second standard well plate 704 for readout and analysis, to which the fluids would drain or be transferred from the microfluidic platform 502. The readout and analysis can be accomplished by an automated reader.

Figure 8:
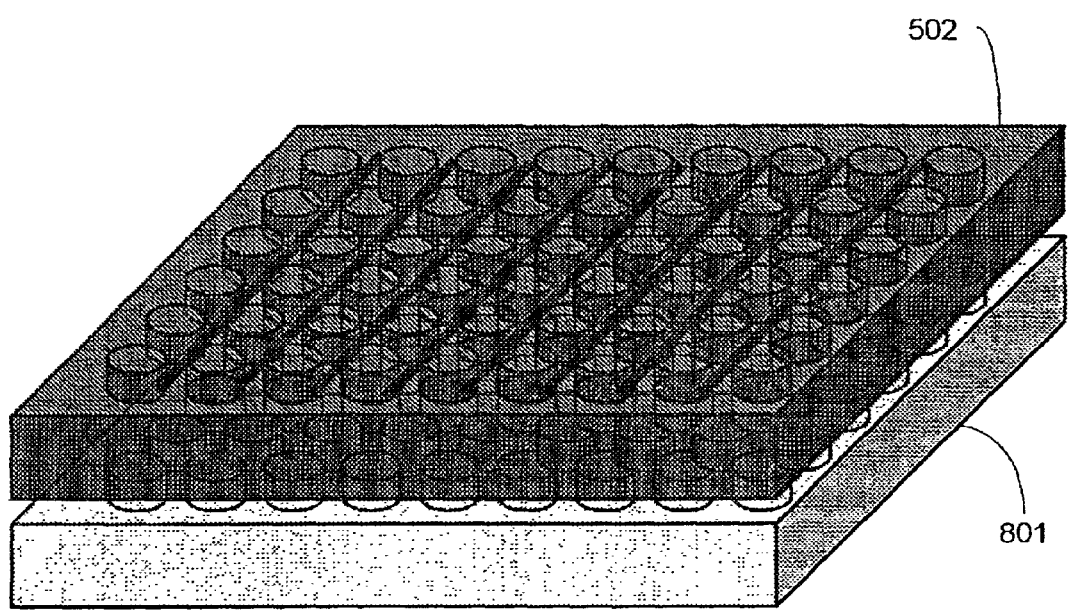
FIG. 8 illustrates a semi-integrated microfluidic platform, according to an embodiment of the invention.
Figure 9:
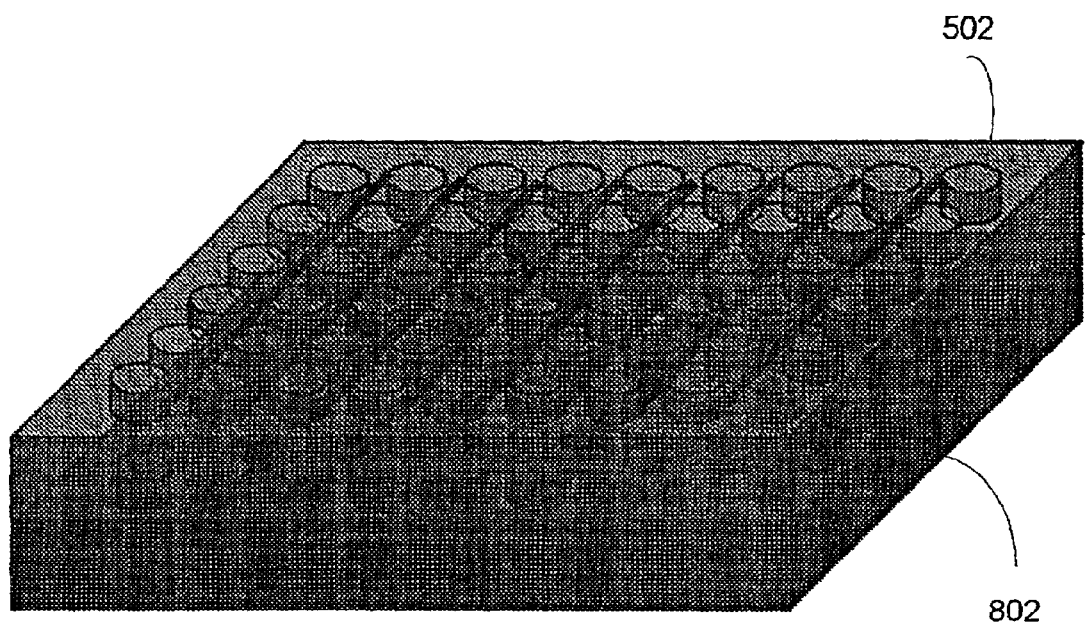
FIG. 9 illustrates a fully-integrated microfluidic platform, according to an alternative embodiment of the invention.

FIGS. 8 and 9 illustrate alternative arrangements for a process combining a microfluidic platform card and standard well plate. FIG. 8 shows a semi-integrated work flow system for carrying out a microfluidic process. A microfluidic card 502 is used for performing an initial reaction, much like the first standard well plate 702 in FIG. 7, and a microfluidic operation. The microfluidic card 502 is then contacted with a standard well plate 801. In one embodiment, the microfluidic card 502 is placed on top of the standard well plate 801. The contact enables removal of the fluids from the microfluidic card 502 and transfer to the well plate 801. The card 502 is removed, and readout can be executed.

FIG. 9 shows a filly integrated system having a microfluidic card 502 permanently, or semi-permanently, connected to a standard well plate 802. The system can be used for performing the initial reaction, including fluid deposition, the microfluidic operation, such as extraction or separation, for example, and the readout or analysis process.

Other arrangements, configurations and methods for executing a block cipher routine should be readily apparent to a person of ordinary skill in the art. Other embodiments, combinations and modifications of this invention will occur readily to those of ordinary skill in the art in view of these teachings. Therefore, this invention is to be limited only be the following claims, which include all such embodiments and modifications when viewed in conjunction with the above specification and accompanying drawings.

What is claimed is:

1. A microfluidic device, comprising:
   a well plate comprising a plate and an array of wells formed on or in the plate; and a microfluidic structure adapted for contact with the well plate and adapted to provide parallel flow of plural fluids in at least one channel, comprising at least one microfluidic circuit, with each circuit having at least one part hole which is in fluid communication with at least one well of the well plate.

2. The device of claim 1, wherein the microfluidic circuit is an H-Filter.

3. The device of claim 2, wherein the H-Filter includes at least two inlets and a microfluidic channel connected to the inlets.

4. The device of claim 3, wherein a first inlet is connected to a first well, and a second inlet is connected to a second well.

5. The device of claim 4, wherein the first inlet is configured to provide a first fluid from the first well to the microfluidic channel, and the second inlet is configured to provide a second fluid to the microfluidic channel in parallel with the first fluid.

6. The device of claim 2, wherein the H-Filter includes a microfluidic channel and at least two outlets connected to the channel.

7. The device of claim 6, wherein a first outlet is connected to a first well, and a second outlet is connected to a second well.

8. The device of claim 7, wherein the first outlet and the second outlet are configured to receive a portion of one or more fluids flowing from the microfluidic channel.

9. The device of claim 2, wherein the H-Filter includes at least one inlet, a microfluidic channel connected to the inlet, and at least one outlet connected to the channel.

10. The device of claim 9, wherein the at least one inlet is connected to a first well, and the at least one outlet is connected to a second well.

11. The device of claim 1, wherein one of the wells connected by the microfluidic circuit has a bottom that is higher than the at least one other well.

12. The device of claim 1, wherein a pattern of the array of wells conforms to one of a 12-, 24-, 48-, 96-, 192-, 384-, or 1536-well plate format.

13. The device of claim 1, wherein the microfluidic circuit connects at least four of the wells.

14. The device of claim 1, further comprising two or more microfluidic circuits, each microfluidic circuit connecting at least two of the wells.

15. A system for performing a microfluidic process, comprising:
 a well plate comprising an array of wells formed on or in the first plate; and
 a microfluidic card comprising an array of microfluidic circuits, each circuit having at least one port hole, the card being sized and adapted for contact with the well plate such that the at least one port hole of each circuit is connected to at least one well.

16. The system of claim 15, wherein each well has a volume that is partially defined by a bottom.

17. The system of claim 16, wherein at least one well in the array has a larger volume than at least one other well.

18. The system of claim 16, wherein at least one well in the array has a lower bottom than at least one other well.

19. The system of claim 16, wherein the at least one port hole of each microfluidic circuit is connected to the bottom of a well.

20. A microfluidic device, comprising:
 a well plate comprising a plate and an array of wells formed on or in the plate
 a well plate comprising a plate and an array of wells formed on or in the plate; and
 a microfluidic structure connecting at least two of the wells,
 wherein one of the wells connected by the microfluidic structure has a bottom that is higher than at least one other well.

* * * * *